United States Patent
Ebers

Patent Number: 5,715,814
Date of Patent: Feb. 10, 1998

[54] RESPIRATION MASK

[75] Inventor: Manfred Ebers, Hamburg, Germany

[73] Assignee: Gottlieb Weinmann Geräte für Medizin und Arbeitsschutz GmbH & Co., Hamburg, Germany

[21] Appl. No.: 572,754

[22] Filed: Jul. 14, 1995

[30] Foreign Application Priority Data

Jul. 15, 1994 [DE] Germany .................. 9411495 U

[51] Int. Cl.⁶ .......................................... A61B 7/10
[52] U.S. Cl. .................... 128/206.18; 128/206.24; 128/206.26
[58] Field of Search ................ 128/206.18, 206.24, 128/206.25, 206.26

[56] References Cited

U.S. PATENT DOCUMENTS

| | | | |
|---|---|---|---|
| 1,105,127 | 7/1914 | Dräger | 128/206.24 |
| 2,435,721 | 2/1948 | Lehmann | 128/206.24 |
| 2,540,567 | 2/1951 | Bennett | 128/206.26 |
| 2,875,759 | 3/1959 | Galleher, Jr. | 128/206.24 |
| 2,877,764 | 3/1959 | Galleher, Jr. | 128/206.24 |
| 3,052,887 | 9/1962 | Sockel et al. | 128/206.24 |
| 4,907,584 | 3/1990 | McGinnis | 128/206.24 |

FOREIGN PATENT DOCUMENTS 4212259  1/1993  Germany .

*Primary Examiner*—Aaron J. Lewis
*Attorney, Agent, or Firm*—Robert W. Becker & Assoc.

[57] ABSTRACT

An individual mask for artificial respiration of a patient has a mask body bridging the nose of the patient at least in the area of the nostrils. The mask body has a hollow bead filled with an elastically yielding material for shaping the bead to match the contour of the patients face. The mask body also has a connector for connecting thereto a gas inlet line. To the mask body securing straps may be attached. An elastic film is connected to the bead and bridges a side of the mask body facing the patents face such that an interior space is delimited by the film and the mask body. The film has a cutout for introducing into the interior space the nose of the patent. The film is preferably made of a breathable and watervapor-permeable material.

3 Claims, 1 Drawing Sheet

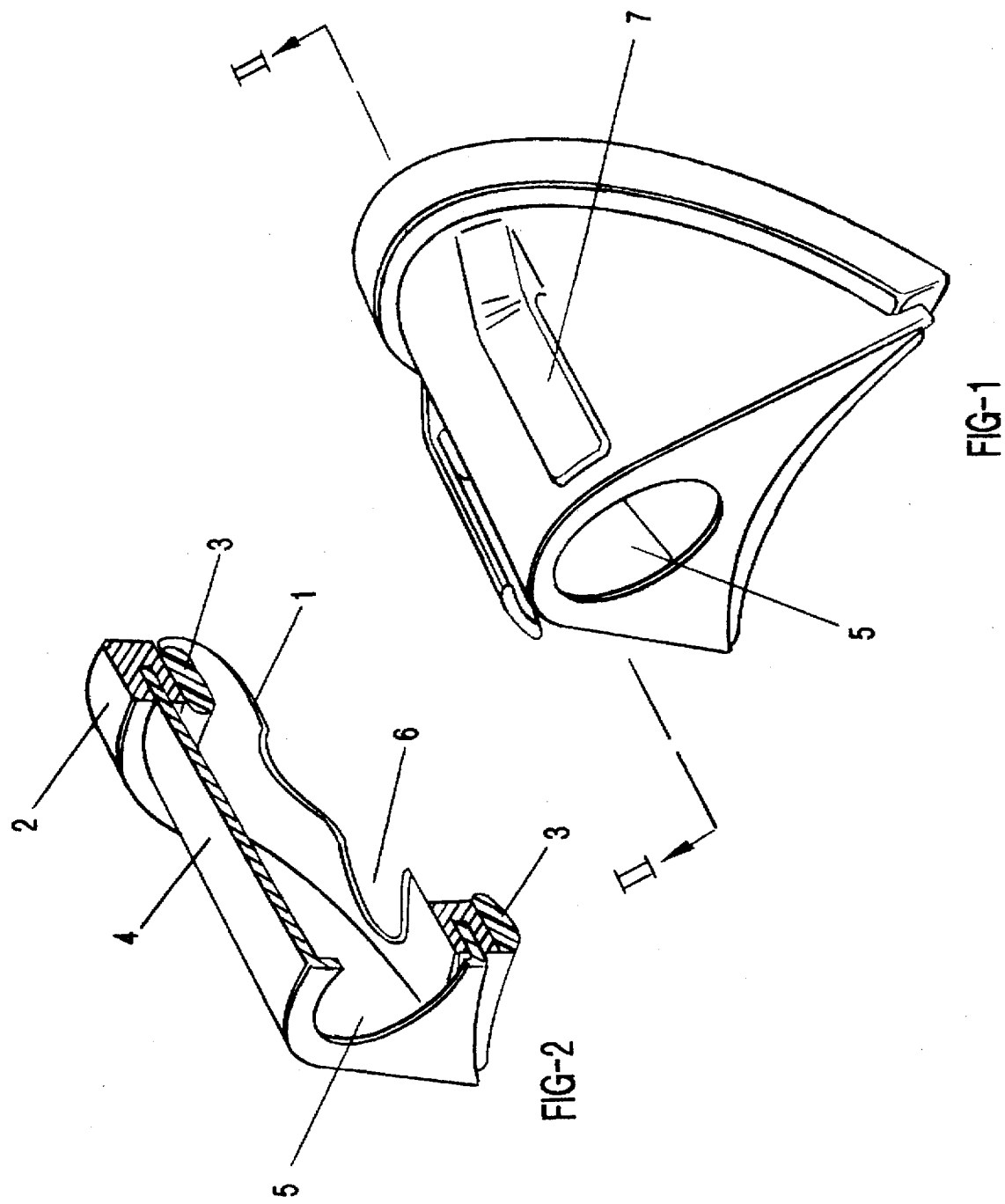

RESPIRATION MASK

BACKGROUND OF THE INVENTION

The present invention relates to an individual mask for artificial respiration of a patient with a mask body bridging the nose of the patient at least in the area of the nostrils and having a hollow bead filled with an elastically yielding material for shaping the bead to match the contour of the patients face. To the mask body at least one gas inlet line is connectable. Securing straps may be attached to the mask body.

Such mass-produced masks are known from German Patent 4 212 259. For adapting the bead which serves as a sealing between the face and the mask and is in the form of a hollow body, the hollow body is filled with a liquid or paste-like plastic material that cures to be form-stable and elastically yielding. Subsequently, the mask is placed onto the face of the patient whereby the still soft and elastic plastic material and thus the sealing surface of the bead is adapted to the contour of the face of the patient. Despite this individual adaptation of the sealing surface to the contour of the face of the patient a complete sealing between the edge of the mask and the face can only be achieved when the respiration mask is pressed with a certain pressure onto the face of the patient which is bothersome for a frequent and long-term use of such respiration masks, for example, for treatment of sleep apnea. Even though small leaks do not impair the effectiveness of artificial respiration, the gases which leak from the mask may result in other illnesses such as conjunctivitis or may be disturbing to the patient because a constant stream of air is felt.

It is therefore an object of the present invention to improve the comfort of such a mask as well as to improve the sealing action between the face of the patient and the respiration mask.

SUMMARY OF THE INVENTION

An individual mask for artificial respiration of a patent according to the present invention is primarily characterized by:

- a mask body bridging the nose of the patient at least in the area of the nostrils;
- the mask body comprising a hollow bead filled with an elastically yielding material for shaping the bead to match the contour of the patents face;
- the mask body further comprising a connector for connecting there to a gas inlet line;
- the mask body having means for attaching thereto securing straps;
- the bead comprising an elastic film bridging a side of the mask body facing the patients face such that an interior space is delimited by the film and the mask body; and
- the film having a cutout for introducing into the interior space the nose of the patient.

Advantageously, the film is comprised of a breathable and watervapor-permeable material. Preferably, the film has an uneven surface.

According to the present invention, the respiration mask is provided with a thin elastic film connected to the bead which bridges the side of the mask body that is facing the face of the patient and which is provided with a cutout for the nose of the patient to be introduced into the interior space defined by the film and the mask body.

The film which bridges the side of the mask body facing the face of the patient is forced against the face of the patent and the nose of the patent when the mask is put onto the patents face due to the pressure of the respiration gas. In this manner, a sealing with a large surface area is provided so that, due to the optimal seating and matching properties of the mask resulting from the individual adaptation of the bead to the contour of the face of the patient, the mask must not be forced with securing straps onto the face of the patient but is simply held in its position on the face of patient. This increased comfort achieved by reducing the pressure applied onto the mask and the face of the patient during application of the mask can be further improved according to the present invention by providing the film in the form of a breathable and watervapor-permeable material such as a synthetic block copolymer and/or by providing the film with an uneven (rough) surface such that sticking of the mask to the facial skin of the patient is prevented without impairing the sealing function of the mask. A micro liquid circulation between film and face is possible.

BRIEF DESCRIPTION OF THE DRAWINGS

The object and advantages of the present invention will appear more clearly from the following specification in conjunction with the accompanying drawings, in which:

FIG. 1 shows a schematic perspective view of the inventive respiration mask; FIG. 2 shows a cross-section along the line II—II of FIG. 1.

DESCRIPTION OF PREFERRED EMBODIMENT

The respiration mask of the present invention is comprised of a mask body 4 with a bore (connector) 5 for connecting thereto a respiration gas inlet line (not represented). The mask has scanning elements 7 for securing it with non-represented securing straps to the head of the patient. At the free rim of the mask body 4 a bead 2 with integrated hollow body 3 made of an elastic material, preferably rubber, is connected. The hollow body 3 of this bead 2 which rests on the face of a patent (not represented), is filled with a material that when cured provides for a form-stable and elastically yielding plastic material. A thin elastic skin 1 is secured to the bead 2 which bridges the side of the mask body 4 that faces the face of the patient and which is provided with a cutout 6 for introducing the nose of the patient into the interior space delimited by the mask body 4 and the film 1.

The present invention is, of course, in no way restricted to specific disclosure of the specification, examples, and drawings, but also encompasses any modifications within the scope of the appemdent claims.

What I claim is:

1. An individual mask for artificial respiration of a patient, said mask comprising:

- a mask body bridging a nose of a patient at least in the area of a patient's nostrils;
- said mask body comprising a hollow bead filled with an elastically yielding material for shaping said bead to match a contour of a patient's face;
- said mask body further comprising a connector for connecting thereto a gas inlet line;
- said mask body having means for attaching thereto securing straps;

said bead comprising an elastic film substantially bridging sides of said mask body facing a patient's face and forming an interior space delimited by said film and said mask body; and said film having a cutout for introducing into said interior space a patient's nose.

2. A mask according to claim 1, wherein said film is comprised of a breathable and water vapor-permeable material.

3. A mask according to claim 1, wherein said film has an uneven surface.

* * * * *